United States Patent [19]

Powers et al.

[11] Patent Number: 5,681,821
[45] Date of Patent: Oct. 28, 1997

[54] FLUORESCENT 1-PEPTIDYLAMINOALKANEPHOSPHONATE DERIVATIVES

[75] Inventors: James C. Powers, Atlanta, Ga.; Ahmed S. Abuelyaman, St. Paul, Minn.

[73] Assignee: Georgia Tech Research Corp., Atlanta, Ga.

[21] Appl. No.: 324,809

[22] Filed: Oct. 18, 1994

[51] Int. Cl.$^6$ .................................................. A61K 38/05
[52] U.S. Cl. ........................ 514/19; 514/18; 514/7; 530/331; 435/4
[58] Field of Search ..................... 514/18, 19, 7; 530/331

[56] References Cited

U.S. PATENT DOCUMENTS

| | | | |
|---|---|---|---|
| 4,314,936 | 2/1982 | Yaron | 260/112.5 |
| 5,164,300 | 11/1992 | Marshall | 435/23 |

OTHER PUBLICATIONS

Meldal Analy & Chem 195, 141, 1991.
Oleksyszen Biochem Biophys Res Comm 161, 143, 1989.
Synthesis of New Phosphonate Inhibitors of Serine Proteases, Fastrez, Jespers, Lison, Renard, and Sonveaux, Tetrahedron Letters, vol. 30, No. 49, pp. 6861–6864, 1989.

Synthesis of Phosphonopeptides as Thrombin Inhibitors, Wang, Taylor, Mical, Spitz, and Reilly, Tetrahedron Letters, vol. 33, No. 50, pp. 7667–7670, 1992.

Inhibition of Chymotrypsin by Phosphonate and Phosphonamidate Peptide Analogs, Bartlett and Lamden, Bioorganic Chemistry 14, 356–377 (1986).

Irreversible Inhibition of Serine Proteases by Peptide Derivatives of ($\alpha$-Aminoalkyl) Phosphonate Diphenyl Esters, Oleksyszyn and Powers, Biochemistry, 1991, 30.

Novel Amidine–Containing Peptidyl Phosphonates as Irreversible Inhibitors for Blood Coagulation and Related Serine Proteases, Oleksyszyn, Boduszek, Kam, and Powers, Journal of Medicinal Chemistry, 1994.

Aminoalkylphosphonofluoridate Derivatives: Rapid and Potentially Selective Inactivators of Serine Peptidases, Lamden and Bartlett (1983).

Primary Examiner—Robert J. Hill, Jr.
Assistant Examiner—David Lukton
Attorney, Agent, or Firm—Deveau, Colton & Marquis

[57] ABSTRACT

Fluorescent 1-peptidylaminoalkanephosphonate derivatives, and their use in detecting and studying the distribution of serine proteases in cells and biological systems.

20 Claims, No Drawings

FLUORESCENT 1-PEPTIDYLAMINOALKANEPHOSPHONATE DERIVATIVES

BACKGROUND OF THE INVENTION

1. Field of the Invention

This invention relates to a novel class of fluorescent peptidyl derivatives of aromatic diesters of 1-aminoalkanephosphonic acid useful for selectively inhibiting elastases, selectively inhibiting chymotrypsin-like enzymes, selectively inhibiting trypsin-like enzymes or for generally inhibiting serine proteases of many classes.

2. Description of the Related Art

Serine proteases play critical roles in several physiological processes such as digestion, blood coagulation, complement activation, fibrinolysis, viral infection, fertilization, and reproduction. Serine proteases are not only a physiological necessity, but also a potential hazard if they are not controlled. Uncontrolled proteolysis by elastases may cause pancreatitis, emphysema, rheumatoid arthritis, bronchial inflammation and adult respiratory distress syndrome. Human polymorphonuclear leukocyte elastase may also be involved in blistering. Accordingly, potent and specific inhibitors of these proteases tagged with fluorescent molecules can be used to detect, localize, and quantify these enzymes in different types of cells and biological systems. Serine proteases inhibited by these fluorescent compounds can be detected at the single cell level.

Many classes of phosphorus containing compounds have been prepared for use as inhibitors of serine proteases. One useful class reported by Oleksyszyn and Powers are peptidyl derivatives of α-aminoalkylphosphonate diphenyl esters (Irreversible Inhibition of Serine Proteases by Peptide Derivatives of (α-aminoalkyl)phosphonate Diphenyl Esters, Oleksyszyn, J. and Powers, J. C., *Biochemistry*, 1991, 30, 485–493). Other members of the class were described by Bartlett, P. A. and Lamden, L. A., *Bioorg. Chem.*, 1986, 14, 356–377 and Lamden, L. A. and Bartlett, P. A., *Biochem. Biophys. Res. Commun.*, 1983, 112, 1085–1090. These compounds are useful inhibitors for the serine proteases elastases, chymotrypsin, chymotrypsin-like, trypsin, trypsin-like, blood coagulation enzymes, kallikrein, plasmin, thrombin, and granzymes. Another class of diphenyl peptide phosphonate esters was published by Oleksyszyn et al., 1994 (Novel Amidine-Containing Peptidyl Phosphonates as Irreversible Inhibitors for Blood Coagulation and Related Serine Proteases Oleksyszyn, J., Boduszek, B., Kam, C.-M., and Powers, J. C., *J. Med. Chem.* 1994, 37, 226–231). This class included peptides with C-terminal phosphonate residues related to ornithine, lysine, arginine, or containing a C-terminal diphenyl ester of α-amino-α-(4-amidinophenyl)methanephosphonate ((4-AmPh)Gly$^P$(OPh)$_2$) or α-amino-α-(4-amidinophenylmethyl)methanephosphonate ((4-AmPhe)$^P$(Oph)$_2$). These peptide phosphonates are specific and potent inhibitors of trypsin, thrombin, kallikrein, trypsin-like enzymes, coagulation enzymes, and granzymes. A few other arginine and ornithine analogs and peptidyl phosphonates containing (α-amino-γ-methoxybutyl)phosphonyl or (α-amino-n-hexyl)phosphonyl residues at the $P_1$ site have been reported to be inhibitors of trypsin and thrombin (Fastrez et al., *Tetrahedron Lett.*, 1989, 30, 6861–6864; Cheng et al., *Tetrahedron Lett.*, 1991, 32, 7333–7336; Wang et al., *Tetrahedron Lett.*, 1992, 33, 7667–7670; and Hamilton et al., *Tetrahedron Lett.*, 1993, 34, 2847–2850). None of the diphenyl peptide phosphonate esters mentioned above has fluorescent label attached to it. Tagging these inhibitors with fluorescent labels will render them excellent tools for studying the distribution of serine proteases as well as measuring their quantities in natural killer cells, lymphocyte cells, and all other types of cells and biological systems.

BRIEF SUMMARY OF THE INVENTION

We have found that diphenyl 1-pepidylaminoalkanephosphonate esters tagged with fluorescent groups such as fluorescein or sulforhodamine 101 are potent inhibitors of elastases, chymases, and other serine proteases. These fluorescent compounds are made by coupling fluorophores to peptidylphosphonates using spacer groups between the peptide and the fluorophore. The spacer groups are inserted in order to prevent unfavorable steric interactions between the fluorophore and the active site of the protease. These compounds can be used to irreversibly label discrete granule-like regions of the natural killer (NK) cells. These fluorescent peptide phosphonates can be used to selectively inhibit serine proteases within whole cells. These fluorescent compounds can also be used to localize serine proteases inside cellular granules. These fluorescent compounds can also be used to selectively or generally inhibit serine proteases either in vitro or in biological systems. The properties of these fluorescent compounds indicate that they will be excellent tools for the study of the distribution of serine proteases in lymphocytes and their role during cytotoxic T-lymphocyte killing. Use of these inhibitors with different peptide sequences with varying specificities and different fluorophores will allow the simultaneous detection of different proteases in cytotoxic lymphocytes as well as in other cells and biological systems.

It is an object of this invention to find a novel group of specific fluorescent inhibitors for elastase, chymotrypsin, trypsin, and other serine proteases of similar substrate specificity and for serine proteases in general. Inhibitors are compounds that can reduce or eliminate the catalytic activity of the enzyme. Trypsin and trypsin-like enzymes normally cleave peptide bonds in proteins and peptides where the amino acid residue on the carbonyl side of the split bond ($P_1$ residue) is Lys, or Arg. Elastase and elastase-like enzymes, on the other hand, cleave peptide bonds where the $P_1$ amino acid is Ala, Val, Ser, Leu and other similar amino acids. Chymotrypsin and chymotrypsin-like enzymes hydrolyze peptide bonds where $P_1$ amino acid is Trp, Tyr, Phe, Met, Leu or other amino acid residues which contain aromatic or large alkyl side chains. All of the above enzymes have extensive secondary specificity and recognize amino acid residues removed from the $P_1$ residue.

It is a further object of this invention to define new fluorescent protease inhibitors, especially inhibitors for chymotrypsin and chymotrypsin-like enzymes, elastases, blood coagulation enzymes, tryptases, trypsin-like enzymes, kallikrein, and granzymes. Such inhibitors could be used to identify and localize new proteolytic enzymes encountered in research. The inhibitors of this invention would be useful for studying the role and the distribution of serine proteases found in cytotoxic T lymphocyte and natural killer cells. These inhibitors are useful for controlling, detecting, and measuring the active serine proteases involved in tumor invasion, blood coagulation and various inflammatory conditions mediated by serine proteases. The inhibitors of this invention would be useful for studying the distribution and role of natural killer and cytotoxic lymphocyte serine proteases.

It is yet another object of this invention to define a novel group of specific inhibitors useful in vitro for inhibiting trypsin, elastase, chymotrypsin and other serine proteases of similar specificity. These inhibitors can be used in research to detect and measure undesired serine proteases found in all cells, tissues, and fluids.

These and other objects are accomplished by the present invention which defines novel fluorescent peptidyl derivatives of aryl diesters of 1-aminoalkanephosphonic acids. These fluorescent phosphonate derivatives are potent inhibitors of serine proteases including chymotrypsin-like enzymes, trypsin-like enzymes, elastase-like enzymes, and other enzymes with other substrate specificities. The fluorescent peptide phosphonates are stable in buffer or plasma, and inhibit the serine proteases to give stable inhibited enzyme derivatives that can easily be detected using confocal microscopy and other ways. The fluorescent peptide phosphonates can be used in both in vitro and in vivo.

DETAILED DESCRIPTION OF THE INVENTION

Fluorescent peptidyl derivatives of aryl diesters of 1-aminoalkanephosphonic acids have been found to be excellent inhibitors of several serine proteases including human leukocyte elastase, porcine pancreatic elastase, bovine chymotrypsin, and bovine trypsin. The fluorescent diesters of 1-peptidylaminoalkanephosphonic acids are analogs of natural α-amino acids and are designated by the generally accepted three letter abbreviations for the amino acid followed by the superscript P. For example diphenyl 1-(6-(5-fluoresceinylthiocarbamoylamino)caproylamino) ethanephosphonate which is related to alanine is abbreviated as FTC-Aca-Ala$^P$(OPh)$_2$. FTC is 5-fluoresceinylthiocarbamoyl and Aca is 6-aminocaproyl.

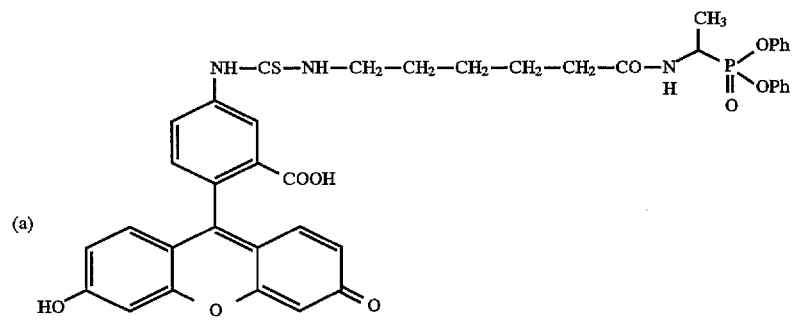

Complete structure of FTC—Aca—Ala$^P$(OPh)$_2$

The novel fluorescent peptidyl phosphonate inhibitors and related compounds contain a fluorophore (Fluor) bonded to the peptidyl phosphonate moiety through a spacer group and they have the following general structure:

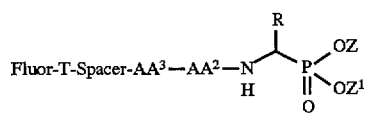

or an acceptable salt, wherein

Fluor is selected from the group consisting of

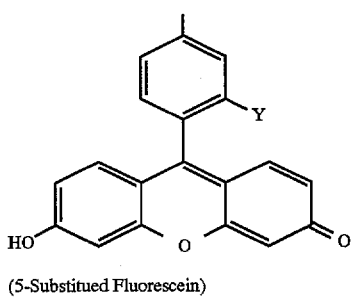

(5-Substitued Fluorescein)

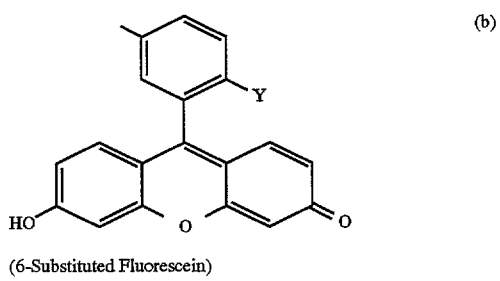

(6-Substituted Fluorescein)

-continued

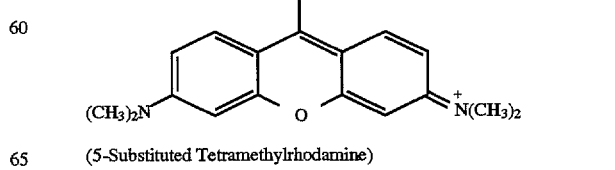

(5-Substituted Tetramethylrhodamine)

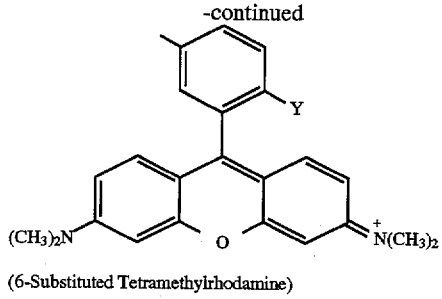
(6-Substituted Tetramethylrhodamine)

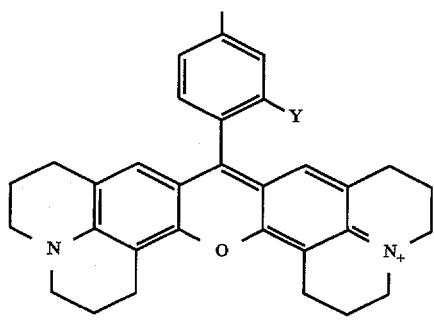
(5-Substituted Texas Red)

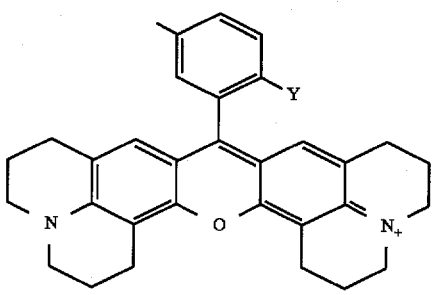
(6-Substituted Texas Red)

(g) an aromatic fluorescent group with an emission maximum of 350 to 700 nm

Y is selected from the group consisting of H, COOH, and $SO_3H$,

T is selected from the group consisting of —NH—CO—, —NH—CS—, —CO—, and —$SO_2$—, Spacer is
  (a) a single bond,
  (b) —NH—$CH_2$—$CH_2$—$CH_2$—$CH_2$—$CH_2$—CO—,
  (c) —NH—$CH_2$—$CH_2$—$CH_2$—$CH_2$—$CH_2$—CO—NH—$CH_2$—$CH_2$—$CH_2$—$CH_2$—$CH_2$—CO—,
  (d) an organic structure which is 3–24 Å long and including a backbone comprising at least one member of the group consisting of —$CH_2$—$CH_2$—, —CO—NH—, —NH—CO—, —$CH_2$—CO—, —$CH_2$—NH—, —NH—$CH_2$—, and —$C_6H_4$—, $AA^3$ and $AA^2$ are the same or different and are selected independently from the group consisting of
  (a) a single bond,
  (b) a blocked or unblocked amino acid residue with the L or D configuration at the α-carbon selected from the group consisting of alanine, valine, leucine, isoleucine, proline, methionine, methionine sulfoxide, methionine sulfone, phenylalanine, tryptophan, serine, threonine, cysteine, tyrosine, asparagine, glutamine, aspartic acid, glutamic acid, lysine, arginine, histidine, phenylglycine, norleucine, norvaline, alpha-aminobutyric acid, citrulline, hydroxyproline, ornithine, and homoarginine, and
  (c) glycine, sarcosine, epsilon-aminocaproic acid, and beta-alanine, R is selected from the group consisting of
  (a) the side chain of a blocked or unblocked amino acid selected from the group consisting of glycine, alanine, valine, leucine, isoleucine, proline, methionine, methionine sulfoxide, methionine sulfone, phenylalanine, tryptophan, serine, threonine, cysteine, tyrosine, asparagine, glutamine, aspartic acid, glutamic acid, lysine, arginine, histidine, phenylglycine, norleucine, norvaline, alpha-aminobutyric acid, citrulline, hydroxyproline, ornithine, and homoarginine, and
  (b) phenyl substituted with B, benzyl substituted with B on the phenyl, B is selected from the group consisting of amidino (—C(=NH)$NH_2$), guanidino (—NH—C(=NH)$NH_2$), isothiureido (—S—C(=NH)$NH_2$), and amino, Z and $Z^1$ are the same or different and are selected independently from the group consisting of phenyl, phenyl substituted with J, phenyl disubstituted with J, and phenyl trisubstituted with J, and J is selected from the group consisting of halogen, $C_{1-6}$ alkyl, $C_{1-6}$ perfluoroalkyl, $C_{1-6}$ alkoxy, $NO_2$, and CN.

The fluorophores used in this invention are those well known in the art of fluorescence. Examples of fluorophores include sulforhodamine (Texas Red), tetramethylrhodamine, rhodamine X, and fluorescein as well as their derivatives and tautomeric forms (see structures below). The fluorescent group can also be any fluorophore which can be attached to the spacer and can emit in the range of 350–700 nm.

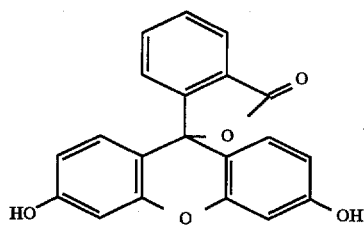
(Lactone Form)

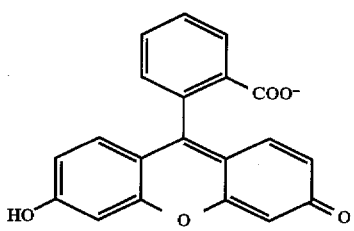
(Open Form)

Fluorescein

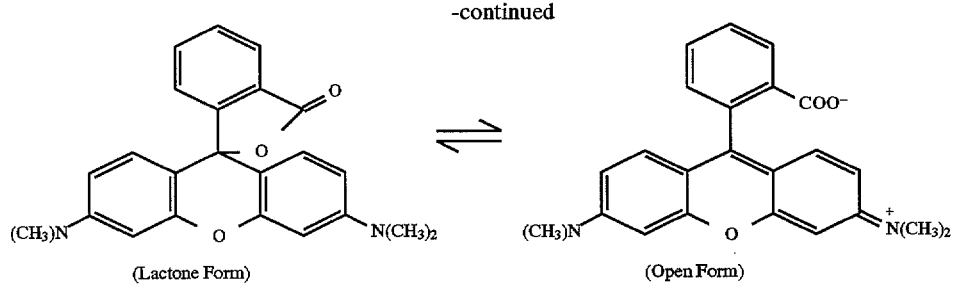

Tetramethylrhodamine

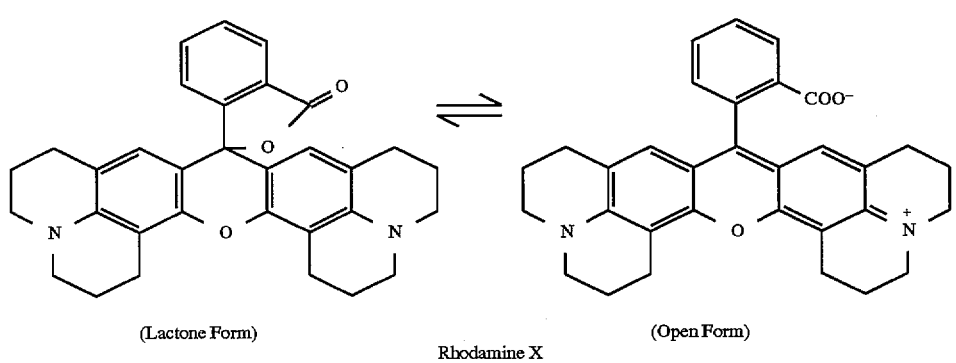

Rhodamine X

Fluorescent peptidyl derivatives of aryl diesters of 1-aminoalkanephosphonic acids inhibit serine proteases by reaction with the active site serine to form phosphonylated enzymes, which due to similarity of phosphorus atom to the tetrahedral intermediate formed during peptide hydrolysis, show remarkable stability. The enzyme catalytic apparatus is required to activate the phosphorus atom for nucleophilic substitution and reaction with enzyme. The activation is mainly due to precise interaction with the $S_1$ pocket of various serine proteases. The following figure shows the reaction course of a phosphonate with a serine protease. The phosphonate first binds to the enzyme (below left) and then reacts to form a covalent bond with the active site serine residue (below right). Slow aging can take place with loss of the phenoxy group (below center).

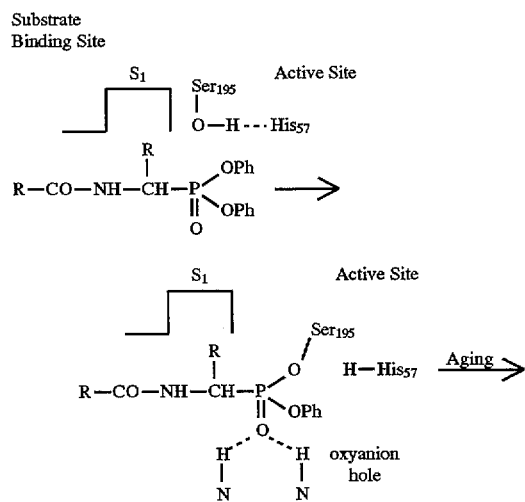

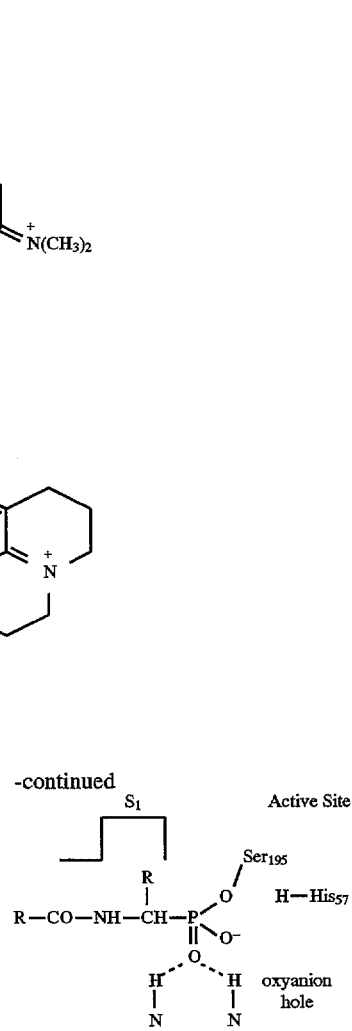

Peptides with a C-terminal phosphonate residue which is an analog of valine (e.g. $Val^P(OPh)_2$) are potent and specific irreversible inhibitors of elastase and elastase-like enzymes. The peptides with C-terminal phosphonate residues related to phenylalanine, other aromatic amino acids or amino acids with long aliphatic side chains are potent and specific inhibitors of chymotrypsin and chymotrypsin-like enzymes. The peptides with C-terminal phosphonate residues related to ornithine, lysine, arginine or containing a C-terminal diphenyl ester of amino(4-amidinophenyl)methanephosphonate (($4$-AmPh)$Gly^P(Oph)_2$) or amino(4-amidinophenylmethyl)methanephosphonate (($4$-AmPhe)$^P$(Oph)$_2$) are specific and potent inhibitors of trypsin and trypsin-like enzymes.

Additional specificity as well as increased activation toward reaction with the enzyme can be introduced into the inhibitor molecule by variation of the amino acid sequence in the peptide portion of the structure. In fact them is a good agreement between the sequence of enzyme substrates such as a peptidyl p-nitroanilides or benzylthioesters and the sequence of an effective peptidyl phosphonate inhibitor. The best inhibitors have the sequence of the best peptidyl p-nitroanilide substrate for a particular enzyme. For example, a potent inhibitor for chymotrypsin and chymotrypsin-like enzymes is FTC-Aca-Phe-Leu-Phe$^P$(OPh)$_2$ (see Table I) which has an amino acid sequence that is analogous to Suc-Phe-Leu-Phe-SBzl, an excellent substrate for these enzymes. With human leukocyte and porcine pancreatic elastases, the best inhibitor (FTC-Aca-Ala-Ala-Ala$^P$(OPh)$_2$) has an amino acid sequence similar to Suc-Ala-Ala-Ala-NA and Boc-Ala-Ala-Ala-NA, two excellent substrates for porcine pancreatic elastase, and to the chloromethyl ketone, Ac-Ala-Ala-AlaCH$_2$Cl, a good inhibitor of human leukocyte elastase. Clearly it is possible to design good phosphonate inhibitors for serine proteases based on the peptide sequences found in other potent reversible and irreversible inhibitors for those same serine proteases reported in the literature. In this application, we disclose methods of attached fluorescent groups to those potent phosphonate inhibitors.

The following compounds are representatives of the invention:

Diphenyl 1-(6-(5-fluoresceneinylthiocarbamoylamino) caproylalanylalanylamino)-3-(methylthio) propanephosphonate Diphenyl 1-(6-(5-fluoresceinylthiocarbamoylamino) caproylalanylalanylamino)ethanephosphonate Diphenyl 1-(6-(5-fluoresceinylthiocarbamoylamino) caproylphenylalanylleucylamino)-2-phenylethanephosphonate Diphenyl 1-(6-(5-fluoresceinylthiocarbamoylamino) caproylamino)(4-amidinophenyl)methanephosphonate Diphenyl 1-(6-(4(or 2)(9-(2,3,6,7,12,13,16,17-octahydro-1H,5H,11H,15H-xantheno(2,3,4-ij:5,6,7-i'j') diquinolizinyl-18-ium))3(or 5)sulfo-1-phenylsulfonamido)caproylphenylalanylleucylamino)-2-phenylethanephosphonate, hydroxide, inner salt.

Enzyme Kinetics

Inactivation rates of serine proteases by fluorescent peptidylphosphonates were measured by the incubation method. In each case the inactivation experiment was preceded by an enzyme assay in which the hydrolysis of peptide p-nitroanilide substrates, catalyzed by chymotrypsin, PPE, HLE, and trypsin was measured in 0.1M Hepes and 0.5M NaCl (0.01M CaCl$_2$ for trypsin), pH 7.5 buffer containing 5–10% Me$_2$SO at 25° C. Stock solutions of substrates were prepared in Me$_2$SO (20 mM) and stored at −20° C. Final substrate concentrations were 0.24 mM. Chymotrypsin activity was assayed with Suc-Val-Pro-Phe-NA. PPE was assayed with Suc-Ala-Ala-Ala-NA. HLE was assayed with MeO-Suc-Ala-Ala-Pro-Val-NA and trypsin was assayed with Z-Arg-NA. The initial rates of hydrolysis were measured at 410 nm ($\epsilon_{410}$=8800 M$^{-1}$cm$^{-1}$) on a Beckman 35 spectrophotometer after 25–50 μL of an enzyme stock solution was added to a cuvette containing 2.0 mL of buffer and 25 μL of substrate.

Each inhibition reaction was initiated by adding a 50 μL aliquot of inhibitor (100–5000 μM in Me$_2$SO) to 0.5 mL of a 0.1M Hepes, 0.5M NaCl (0.01M CaCl$_2$ for trypsin), pH 7.5 buffer containing 50 μL of a stock enzyme solution at 25° C. The enzyme stock solutions were 20 μM chymotrypsin, trypsin, and PPE in 1 mM HCl (pH 3), and 0.4–4 μM HLE in 0.25M NaAc and 1M NaCl at pH 5.5. All the enzyme stock solutions were stored at −20° C. prior to use. Aliquots (25 μL) were withdrawn at various intervals and the residual enzymatic activity was measured spectrophotometrically as described above. Pseudo first-order inactivation rate constants ($k_{obsd}$) were obtained from plots of ln v/v$_o$ vs time and had correlation coefficients greater than 0.98. Each $k_{obsd}$ was calculated from 5–10 activity determinations which extended to 2–3 half lives. Control experiments were carried out in the same way as described above except Me$_2$SO was added in place of the inhibitor solution in Me$_2$SO. The initial rates of substrate hydrolysis did not change during the first 60 minutes of incubation. These initial rates were used as v$_o$ in the calculation of the inhibition rate constants.

Inhibitor Potency

The fluorescent compounds were evaluated as inhibitors of chymotrypsin, PPE, and HLE and were found to be potent and very specific with inactivation rate constants ($k_{obsd}$/(I)) as high as 9,500 M$^{-1}$s$^{-1}$ (Table I). The specificity of these phosphonate inhibitors is dependent upon the amino acid sequence in the tripeptide portion of the inhibitor. In each case, the amino acid sequence was chosen based on the specific sequence of a good substrate or inhibitor for the target enzyme. For example, previous studies showed that human Q31 chymase, cathepsin G, and related chymotrypsin-like enzymes have significant hydrolysis activity toward Suc-Phe-Leu-Phe-SBzl and were potently inhibited by the corresponding peptide chloromethyl ketone, Suc-Phe-Leu-Phe-CH$_2$Cl. The Phe derivative compound (3), which has the same amino acid sequence inhibited chymotrypsin very potently ($k_{obsd}$/(I)=9,500 M$^{-1}$s$^{-1}$ ) and 600 times faster than it inhibited HLE ($k_{obsd}$/(I)=16 M$^{-1}$s$^{-1}$). Chymotrypsin was also inhibited by FTC-Aca-Ala-Ala-Met$^P$(OPh)$_2$ (1) more effectively ($k_{obsd}$/(I)=190 M$^{-1}$s$^{-1}$) than HLE and PPE ($k_{obsd}$/(I)=22 and 13 M$^{-1}$s$^{-1}$, respectively). Likewise, the p-nitroanilide substrates Suc-Ala-Ala-Ala-NA and Boc-Ala-Ala-Ala-NA were hydrolyzed effectively by PPE and peptide chloromethyl ketones such as Ac-Ala-Ala-Ala-Ala-CH$_2$Cl are good inhibitors of HLE. Compound (2), FTC-Aca-Ala-Ala-Ala$^P$(OPh)$_2$, as expected inhibited PPE and HLE with $k_{obsd}$/(I) of 22 and 41 M$^{-1}$s$^{-1}$, respectively, but did not inhibit chymotrypsin.

The presence of the fluorescein fluorophore in these inhibitors resulted in either better or the same inhibitory potency compared to their nonfluorescent analogs. For example, with chymotrypsin, the presence of the fluorophores increased the potency of these inhibitors. The fluoresceinylated Phe analog (3) inhibited chymotrypsin very potently with $k_{obsd}$/(I) of 9500 M$^{-1}$s$^{-1}$, while the nonfluoresceinylated analog, Z-Phe-Leu-Phe$^P$(OPh)$_2$ (7), inhibited chymotrypsin but less potently with $k_{obsd}$/(I) of 110 M$^{-1}$s$^{-1}$. Compound (1), FTC-Aca-Ala-Ala-Met$^P$(OPh)2, was found to be a better inhibitor of chymotrypsin and HLE, $k_{obsd}$/(I) =190 and 22 M$^{-1}$s$^{-1}$ respectively, than Boc-Ala-Ala-Met$^P$ (OPh)$_2$ (5), $k_{obsd}$/(I)=3 and 2 M$^{-1}$s$^{-1}$, respectively. In contrast to FTC enhancement of the inhibitory potency of the chymotrypsin-directed inhibitors with chymotrypsin, the presence of FTC did not alter the efficacy of the elastase-directed inhibitor with the two elastases. FTC-Aca-Ala-Ala-Ala$^P$(OPh)$_2$ (2) and its analog Z-Ala-Ala-Ala$^P$(OPh)$_2$ (6), inhibited HLE with almost equal rate constant values, $k_{obsd}$/(I)=38 and 41 M$^{-1}$s$^{-1}$, respectively. Compound (2) also showed similar efficacy with PPE as compound (6), $k_{obsd}$/(I)=22 and 30 M$^{-1}$s$^{-1}$, respectively. Fluorescent Met and Phe derivatives (1) and (3) are better inhibitors of PPE ($k_{obsd}$/(I)=13 and 16 M$^{-1}$s$^{-1}$, respectively) compared to their nonfluorescent analogs, compounds (5) ($k_{obsd}$/(I)=3 M$^{-1}$s$^{-1}$) and (7) (no inhibition). The fluoresceinylated Ala analog, Compound (2), on the other hand, showed almost the same inhibitory effect with PPE as did its nonfluorescent analog, Z-Ala-Ala-Ala$^P$(OPh)$_2$ (6), $k_{obsd}$/(I)=22 and 30 M$^{-1}$s$^{-1}$, respectively.

Addition of the Texas Red fluorophore resulted in a less effective compound in comparison with an analogous compound with the FTC-fluorophore. The TXR-labeled derivative, TXR-Aca-Phe-Leu-Phe$^P$(OPh)$_2$ (4) showed less inhibition with all three enzymes compared to FTC-Aca-Phe-Leu-Phe$^P$(OPh)$_2$ (3). However, when TXR-Aca-Phe-Leu-Phe$^P$(OPh)$_2$ (4) was compared with nonfluorescent Z-Phe-Leu-Phe$^P$(OPh)$_2$ (7), the effects varied with the different enzymes. Inhibition of chymotrypsin was less with TXR-Aca-Phe-Leu-Phe$^P$(OPh)$_2$ (4) while inhibition of HLE and PPE was greater (Table I).

From the results discussed above, it can be concluded that attaching the fluorophores in these phosphonate inhibitors resulted in either a similar or equal inhibitory potency with HLE and PPE. In the case of chymotrypsin, the presence of the FTC fluorophore increased the potency of these inhibitors substantially, an observation that implies interactions between this fluorophore and chymotrypsin. It is also clear that the specificities of these fluorescent compounds are parallel to those of nonfluorescent analogs and are dependent on the sequences of the peptide portions.

protease inhibitor soybean trypsin inhibitor. In the latter experiments, the cells were fixed and permeabilized before the macromolecular inhibitor was used. Thus the fluorescent phosphonate compounds offer technical advantages over previous approaches. The new reagents also have far greater specificity: soybean trypsin inhibitor inactivated both tryptases and chymases of cytotoxic lymphocytes whereas the FTC-Aca-Ala-Ala-Met$^P$(OPh)$_2$ inactivated RNK-16 chymase and little Asp-ase or tryptase granule protease activities.

Synthesis

The diphenyl 1-aminoalkanephosphonate esters are synthesized from the appropriate aldehyde, benzyl carbamate, and triphenyl phosphite using previously a reported method

TABLE I

Inhibition of Serine Proteases by Fluorescent Peptide Phosphonates[a]

| | | $k_{obsd}/(I)$ $(M^{-1}s^{-1})$ | | |
|---|---|---|---|---|
| Inhibitor | (I) (mM) | Chymotrypsin | PPE | HLE |
| FTC—Aca—Ala—Ala—Met$^P$(Oph)$_2$(1) | 8.3 | 190 | 13 | 22 |
| FTC—Aca—Ala—Ala—Ala$^P$(OPh)$_2$(2) | 8.3 | NI[b] | 22 | 41 |
| FTC—Aca—Phe—Leu—Phe$^P$(OPh)$_2$(3) | 8.3 | 9500 | 16 | 252 |
| TXR—Aca—Phe—Leu—Phe$^P$(OPh)$_2$(4) | 8.3 | 15 | 11 | 96 |
| Boc—Ala—Ala—Met$^P$(OPh)$_2$(5) | 210 | 3 | 3 | 2 |
| Z—Ala—Ala—Ala$^P$(OPh)$_2$(6) | 41.7 | NI | 30 | 38 |
| Z—Phe—Leu—Phe$^P$(Oph)$_2$(7) | 10.4 | 110 | NI | 27 |

[a]Inhibition kinetics were measured in 0.1 M Hepes, 0.5 M NaCl, pH 7.5 buffer, 5–10% Me$_2$SO and at 25° C.
[b]No inhibition after 40 min. of incubation of inhibitor and enzyme. No inhibition was observed with trypsin after one hour of incubation of the enzyme and the inhibitor in 0.1 M Hepes, 0.01 M CaCl$_2$, pH 7.5.

Cell Labeling and Imaging. Cells of the NK line RNK-16 were labeled as live cells, washed, treated with methanol as a fixative and permeabilizing agent, and then examined by confocal microscopy. The cells were treated at 1×10$^7$ cells/mL in RPMI 1640 culture media (Sigma Chemical Co., St. Louis, Mo.) containing 10 mM Hepes with 0.1 mM FTC-Aca-Ala-Ala-Met$^P$(OPh)$_2$ for 30 minutes at 37° C. Control cells were treated with the same volume of DMSO required to deliver the inhibitor (typically 1% final concentration). Cells were then washed several times with phosphate buffered saline (PBS) to remove excess inhibitor. They were suspended overnight in cold 80% methanol to permeabilize the membrane. The cells were washed free of MeOH into PBS and fixed onto poly-L-lysine (Sigma) coated microscope slides using 3% paraformaldehyde. Fixed slides were washed in PBS, coated with Vectashield (Vector Laboratories, Inc., Burlingame, Ca.) to prevent fluorescence fading and topped with a coverslip. Fluorescent laser scanning confocal microscopy was done with a Bio-Rad MRC 600 confocal system utilizing a Zeiss Axiophot microscope and equipped with a mixed-gas argon/krypton ion laser using 488 nm excitation for fluorescein.

Fluorescent peptide phosphonates inactivated and labeled intracellular granzymes. They traversed the membranes of living cells and of their granules and irreversibly labeled the cells for subsequent analyses. The inhibitor FTC-Aca-Ala-Ala-Met$^P$(OPh)$_2$ reacted with distinct, granule-like regions of the cytotoxic lymphocytes cell line RNK-16, similar to granules as observed in living cells by differential interference contrast microscopy. Examination of individual sections through the cells, indicated that these fluorescent regions are interspersed in the cytoplasm. The fluorescent regions had a granule-like morphology similar to that detected by granzyme reactivity with the reversible serine (Diphenyl 1-Aminoalkanephosphonates, Oleksyszyn, J., Subotkowska, L., and Mastalerz, P., Synthesis, 1979, 985–986). For example, H-Phe$^P$(OPh)$_2$, H-Met$^P$(OPh)$_2$, H-Ala$^P$(OPh)$_2$, H-Val$^P$(OPh)$_2$ can be prepared by reaction of phenylacetaldehyde, 3-(methylthio)propionaldehyde, acetaldehyde, 2-methylpropionaldehyde, respectively, with triphenylphosphite, benzyl carbamate, and acetic acid to give the corresponding Cbz-protected amino acid phosphonates (see scheme below) which can be deblocked by treatment with HBr/HOAc or hydrogenolysis. Likewise the chloro derivative, bis(4-chlorophenyl) 1-(N-benyzyloxycarbonylamino)-3-methylthiopropanephosphonate, Cbz-Met$^P$(4-Cl-C$_6$H$_4$O)$_2$ can be prepared from tris(4-chlorophenyl)phosphite, benzylcarbamate, and 3-methylthiopropionaldehyde in the presence of acetic acid.

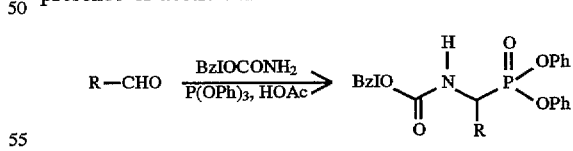

Peptide derivatives can then prepared by sequential coupling of N-blocked amino acids using the DCC coupling method according to the scheme below. For example H-Phe-Leu-Phe$^P$(OPh)$_2$ was prepared by coupling H-Phe$^P$(OPh)$_2$ to Cbz-Leu-OH followed by removal of the Cbz group then coupling to Cbz-Phe-OH and finally removal of the protecting group. H-Ala-Ala-Ala$^P$(OPh)$_2$ and H-Ala-Ala-Met$^P$(OPh)$_2$ were prepared in the same way by coupling H-Ala$^P$(OPh)$_2$ and H-Met$^P$(OPh)$_2$, respectively to Cbz-Ala-OH followed by deblocking, coupling with Cbz-Ala-OH, and deblocking. H-Val-Pro-Val$^P$(OPh)$_2$ was prepared from H-Val$^P$(OPh)$_2$ by coupling with Cbz-Pro-OH, deblocking, coupling with Cbz-Val-OH, and then deblocking.

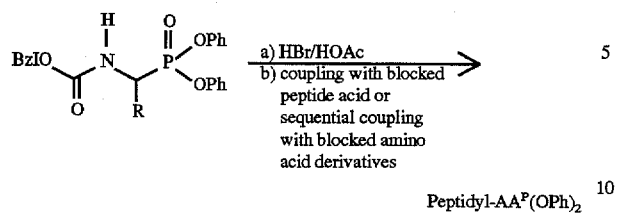

Fluorescein- and Texas Red-labeled diphenyl peptidyl phosphonate esters are made by joining two intermediates: a fluorophore-ε-aminocaproic acid unit and a peptide or amino acid phosphonate. Fluorescein isothiocyanate and Texas Red are coupled to methyl 6-aminocaproate followed by saponification of the ester group to give FTC-Aca-OH and TXR-Aca-OH, respectively, see scheme below. Similar synthetic routes can be used with other fluorescent groups which can be attached to Aca-OMe or other spacer group via $CO_2H$, $SO_3H$, NCS, or NCO functional groups.

Fluor-Aca-peptide phosphonate

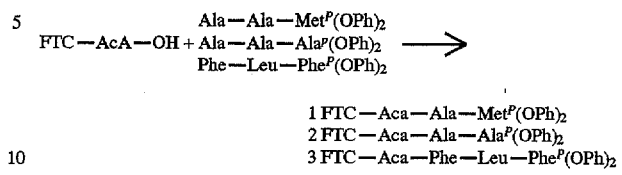

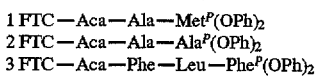

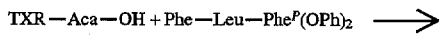

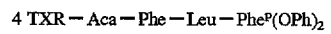

Example of Attachment of the Fluor-Spacer Unit to an Amino Acid Phosphonates

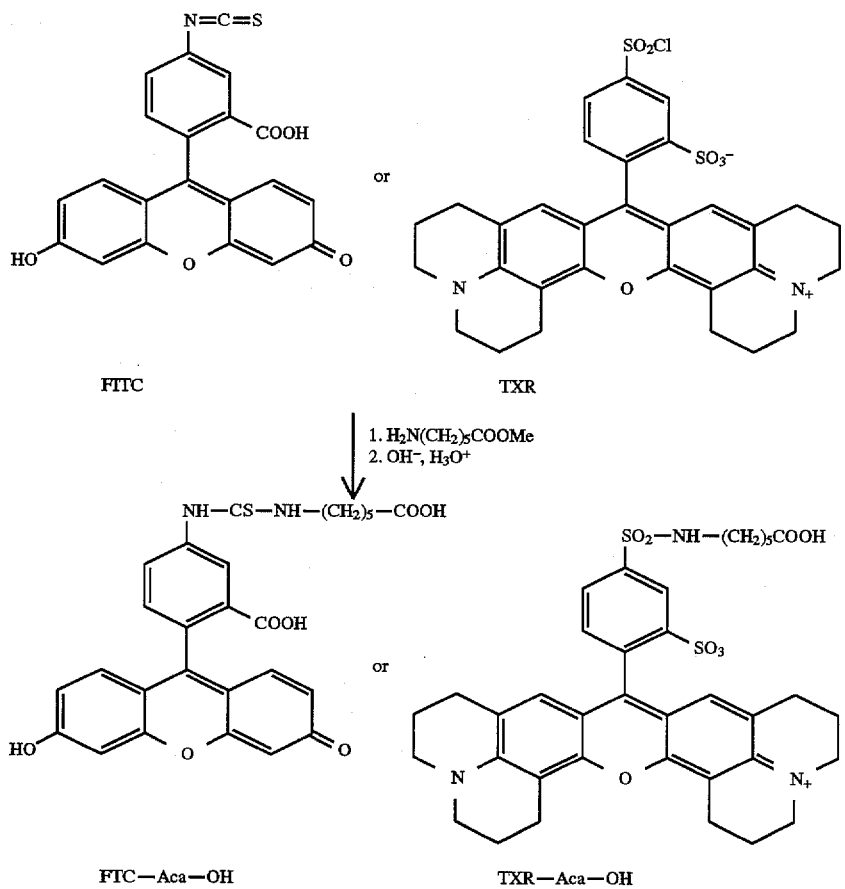

Both intermediates can be coupled to the amino acid or peptide phosphonate unit using the DCC coupling method as shown in the scheme below.

Examples of Attachment of the Fluor-Spacer Units to Peptide Phosphonates

Fluor-Aca unit + peptide phosphonate ⟶

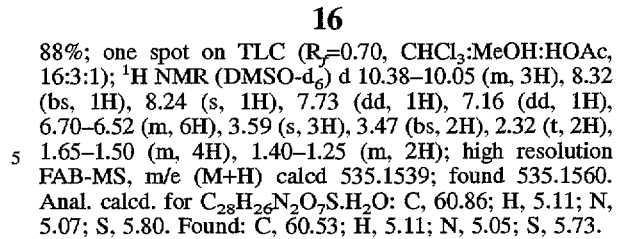
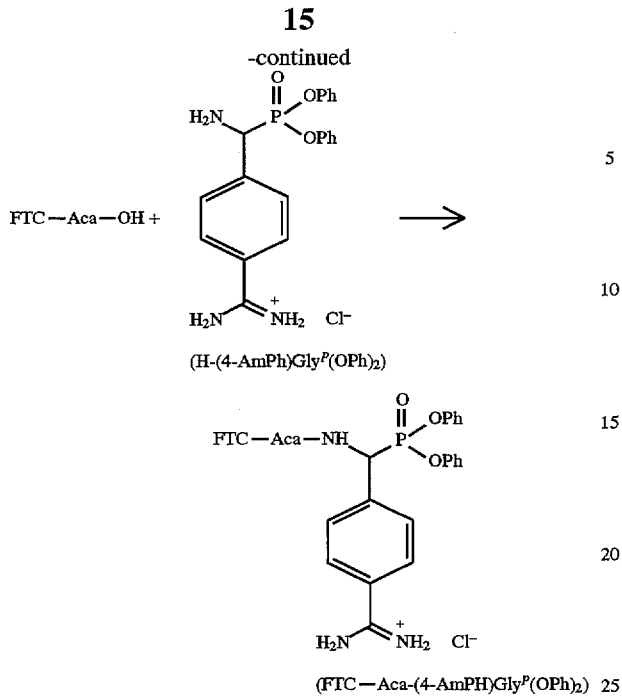

The following examples are given to illustrate the invention and are not intended to limit it in any manner.

GENERAL SYNTHESIS PROCEDURES

5-Fluorescein isothiocyanate (FITC), sulforhodamine 101, 6-aminocaproic acid (Aca), and all common reagents and solvents were purchased from Aldrich Chemical Company, Milwaukee, Wis. Porcine pancreatic elastase (PPE) was obtained from United States Biochemical Corp., Cleveland, Ohio. Human leukocyte elastase (HLE) was obtained from Athens Research and Technology, Inc., Athens, Ga. Hepes was obtained from Research Organics, Inc., Cleveland, Ohio. Bovine trypsin was purchased from Sigma Chemical Company, St. Louis, Mo. Preparative thin-layer chromatography was performed with plates precoated with 2 mm of silica gel G.F. and were obtained from EM Separations, Gibbstown, N.J. 08027. NMR spectra were recorded on a Varian GEMINI 300. Elemental analyses were performed by the Atlantic Microlabs, Atlanta, Ga. Diphenyl 1-(N-dipeptidylamino)alkanephosphonate esters were synthesized as previously described (Oleksyszyn and Powers, *Biochemistry*, 1991, 30, 485–493). The sulfonyl chloride of sulforhodamine 101 (Texas Red) was prepared as previously described (Titus et al., *J. Immunol. Methods*, 1982, 50, 193–204) and was used without further isolation in coupling reactions.

EXAMPLE 1

6-(5-Fluoresceinylthiocarbamoylamino)caproic acid (FTC-Aca-OH)

5-Fluorescein isothiocyanate (0.20 g, 0.51 mmol) was dissolved in 5 mL of DMF. A solution of methyl 6-aminocaproate (0.15 g, 1.03 mmol) in 1 mL of DMF was added at RT, and the mixture was stirred for 0.5 h. The solvent was removed in vacuo. The residue was purified on a silica gel column eluted with $CHCl_3$:MeOH (4:1). Fractions with $R_f$=0.38 were collected and concentrated to give a dark orange oily residue which was triturated with $H_2O$ to give FTC-Aca-OMe as an orange sheet-like solid: yield 88%; one spot on TLC ($R_f$=0.70, $CHCl_3$:MeOH:HOAc, 16:3:1); $^1$H NMR (DMSO-$d_6$) d 10.38–10.05 (m, 3H), 8.32 (bs, 1H), 8.24 (s, 1H), 7.73 (dd, 1H), 7.16 (dd, 1H), 6.70–6.52 (m, 6H), 3.59 (s, 3H), 3.47 (bs, 2H), 2.32 (t, 2H), 1.65–1.50 (m, 4H), 1.40–1.25 (m, 2H); high resolution FAB-MS, m/e (M+H) calcd 535.1539; found 535.1560. Anal. calcd. for $C_{28}H_{26}N_2O_7S \cdot H_2O$: C, 60.86; H, 5.11; N, 5.07; S, 5.80. Found: C, 60.53; H, 5.11; N, 5.05; S, 5.73.

A solution of 1N NaOH (3.0 mL) was added to FTC-Aca-OMe followed by a minimum of MeOH to give a clear solution that was stirred at RT for 1 h. Most of the MeOH was removed in vacuo and the aqueous solution was placed in an ice bath. Drops of concentrated HCl were added with stirring until the mixture became just acidic (pH=3–4). The orange suspension that formed was cooled for 3 additional hours. The solid was isolated by vacuum filtration and dried to give FTC-Aca-OH as an orange solid: yield, 95%; one spot on TLC ($R_f$=0.51, $CHCl_3$:MeOH:HOAc, 16:3:1); $^1$H NMR (DMSO-$d_6$) d 12.00 (bs, 1H), 10.15 (s, 2H), 9.90 (bs, 1H), 8.30 (s, 1H), 8.15 (bs, 1H), 7.80 (d, 1H), 7.20 (d, 1H), 6.75–6.52 (m, 6H), 3.60–3.40 (bs, 2H), 2.25 (t, 2H), 1.62–1.48 (m, 4H), 1.42–1.27 (m, 2H); MS (FAB$^+$) m/e 521 (M+1) Anal. calcd. for $C_{27}H_{24}N_2O_7S \cdot 0.5H_2O$: C, 61.24; H, 4.76; N, 5.29; S, 6.05. Found: C, 61.42; H, 4.58; N, 5.14; S, 6.00.

EXAMPLE 2

Diphenyl 1-(6-(5-Fluoresceinylthiocarbamoylamino) caproylalanylalanylamino)-3-(methylthio) propanephosphonate (FTC-Aca-Ala-Ala-Met$^P$(OPh)$_2$) (General Coupling Procedure)

FTC-Aca-OH (0.13 g, 0.25 mmol) and the hydrochloride of H-Ala-Ala-Met$^P$(OPh)$_2$ (0.13 g, 0.25 mmol) were dissolved in 25 mL DMF followed by addition of 1 equivalent of TEA. The solution was stirred in an ice bath for 15 min, then DCC (0.05 g, 0.25 mmol) was added and the mixture was stirred at 0° C. for 4 h and at RT for 48 h. The solvent was removed in vacuo and the residue was purified on a silica gel column eluted with $CHCl_3$:MeOH (9:1). Fractions containing product were combined and concentrated in vacuo to give a yellow oil that was triturated with water to give a bright yellow solid: yield 25%; $^1$H NMR (DMSO-$d_6$) d 10.15 (s, 2H), 9.95–9.82 (bs, 1H), 8.45 (d, 1H), 8.25 (s, 1H), 8.18–7.98 (m, 3H), 7.73 (d, 1H), 7.49–7.35 (m, 4H), 7.30–7.10 (m, 7H), 6.73–6.52 (m, 6H), 4.89–4.67 (m, 1H), 4.42–4.20 (m, 2H), 3.58–3.42 (bs, 2H), 2.72–2.32 (m, 2H), 2.22–1.92 (m and s, 7H), 1.63–1.42 (m, 4H), 1.38–1.10 (m, 8H); MS (FAB$^+$) m/e 1004 (M+Na). Anal. calcd. for $C_{49}H_{52}N_5O_{11}PS_2 \cdot 1.5H_2O$: C, 58.32; H, 5.49; N, 6.94; S, 6.35. Found: C, 58.43; H, 5.72; N, 6.68; S, 6.01.

FTC-Aca-Met$^P$(OPh)$_2$ can be prepared from FTC-Aca-OH and H-Met$^P$(OPh)$_2$ using the same method. FTC-Aca-Ala-Met$^P$(OPh)$_2$ can be obtained from the reaction of FTC-Aca-OH and H-Ala-Met$^P$(OPh)$_2$. FTC-Aca-Ala-Ala-Met$^P$(4-Cl-$C_6H_4$O)$_2$ can also be prepared from FTC-Aca-OH and H-Ala-Ala-Met$^P$(4-Cl-$C_6H_4$O)$_2$ following the general procedure. Likewise, FTC-Aca-Ala-Ala-Pro-Met$^P$(OPh)$_2$ and FTC-Aca-Ala-Ala-Pro-Met$^P$(4-Cl-$C_6H_4$O)$_2$ can be prepared by the same procedure by coupling FTC-Aca-OH to H-Ala-Ala-Pro-Met$^P$(OPh)$_2$ and H-Ala-Ala-Pro-Met$^P$(4-Cl-C6H$_4$O)$_2$, respectively.

EXAMPLE 3

Diphenyl 1-(6-(5-Fluoresceinylthiocarbamoylamino) caproylalanylalanylamino) ethanephosphonate (FTC-Aca-Ala-Ala-Ala$^P$(OPh)$_2$)

The general procedure for compound 1 was used, starting with H-Ala-Ala-Ala$^P$(OPh)$_2$. Crude product was purified on a silica gel preparative TLC plate using CHCl$_3$:MeOH (85:15) as the eluant solvent to give a yellow solid: yield 35%; $^1$H NMR (DMSO-d$_6$) d 10.30–10.05 (bs, 2H), 9.98–9.85 (bs, 1H), 8.55 (t, 1H), 8.25 (s, 1H), 8.18–7.95 (m, 3H), 7.75 (d, 1H), 7.48–7.32 (m, 4H), 7.28–7.08 (m, 7H), 6.75–6.52 (m, 6H), 4.78–4.55 (m, 1H), 4.45–4.18 (m, 2H), 3.58–3.38 (m, 2H), 2.12 (t, 2H), 1.62–1.05 (m, 15H); MS (FAB$^+$) m/e 921 (M). Anal. calcd. for C$_{47}$H$_{48}$N$_5$O$_{11}$PS.H$_2$O: C, 60.06; H, 5.37; N, 7.50; S, 3.40. Found: C, 60.04; H, 5.35; N, 7.36; S, 3.39.

Using the same procedure, FTC-Aca-Ala$^P$(OPh)$_2$ and FTC-Aca-Ala-Ala$^P$(OPh)$_2$ can be prepared from FTC-Aca-OH and H-Ala$^P$(OPh)$_2$ and H-Ala-Ala$^P$(OPh)$_2$, respectively. FTC-Aca-Ala-Ala-Ala$^P$(4-Cl-C$_6$H$_4$O)$_2$ can also be prepared from the reaction of FTC-Aca-OH and H-Ala-Ala-Ala$^P$(Oph)$_2$, FTC-Aca-Ala-Ala-Val$^P$(OPh)$_2$ can be prepared from FTC-Aca-OH and H-Ala-Ala-Val$^P$(Oph)$_2$, FTC-Aca-Ala-Ala-Val$^P$(4-Cl-C$_6$H$_4$O)$_2$ can be obtained from the reaction between FTC-Aca-OH and H-Ala-Ala-Val$^P$(OPh)$_2$, FTC-Aca-Val-Pro-Val$^P$(OPh)$_2$ can be prepared from FTC-Aca-OH and H-Val-Pro-Val$^P$(Oph)$_2$, FTC-Aca-Val-Pro-Val$^P$(4-Cl-C$_6$H$_4$O)$_2$ can be prepared from FTC-Aca-OH and H-Val-Pro-Val$^P$(4-Cl-C$_6$H$_4$O)$_2$, FTC-Aca-Ala-Ala-Nva$^P$(OPh)$_2$ can be prepared from coupling FTC-Aca-OH to H-Ala-Ala-Nva$^P$(OPh)$_2$, and FTC-Aca-Ala-Ala-Nva$^P$(4-Cl-C$_6$H$_4$O)$_2$ can be prepared by coupling FTC-Aca-OH to H-Ala-Ala-Nva$^P$(4-Cl-C$_6$H$_4$O)$_2$.

EXAMPLE 4

Diphenyl 1-(6-(5-Fluoresceinylthiocarbamoylamino) caproylphenylalanylleucylamino)-2-phenylethanephosphonate (FTC-Aca-Phe-Leu-Phe$^P$(OPh)$_2$)

The general procedure for compound 1 was used, starting with H-Phe-Leu-Phe$^P$(OPh)$_2$. Yield 36%; $^1$H NMR (DMSO-d$_6$) d 10.15 (s, 2H), 9.85 (bs, 1H), 8.87 (d, 1H), 8.77 (d, 1H), 8.25 (s, 1H), 8.10–7.90 (m, 3H), 7.75 (d, 1H), 7.45–7.05 (m, 21H), 6.72–6.52 (m, 6H), 4.92–4.75 (m, 1H), 4.62–4.32 (m and m, 2H), 3.50–2.55 (m, 6H), 2.09–1.92 (m, 2H), 1.60–0.90 (m, 9H), 0.85–0.65 (m, 6H); MS (FAB$^+$) m/e 389.9 (100%, M$^+$-fluoresceinyl-NHCS), 1116 (20%, M+1). Anal. calcd. for C$_{62}$H$_{62}$N$_5$O$_{11}$PS.H$_2$O: C, 65.66; H, 5.69; N, 6.17; S, 2.82. Found: C, 65.98; H, 5.68; N, 6.21; S, 2.80.

FTC-Aca-Phe$^P$(OPh)$_2$ can be obtained from the reaction of FTC-Aca-OH and H-Ph$^P$(OPh)$_2$ using the procedure above. FTC-Aca-Pro-Phe$^P$(OPh)$_2$ and FTC-Aca-Leu-Phe$^P$(OPh)$_2$ can also be prepared from coupling FTC-Aca-OH with H-Pro-Phe$^P$(OPh)$_2$ and H-Leu-Phe$^P$(OPh)$_2$, respectively. FTC-Aca-Phe-Leu-Phe$^P$(4-Cl-C$_6$H$_4$O)$_2$ can be prepared following the same procedure from FTC-Aca-OH and H-Phe-Leu-Phe$^P$(4-Cl-C$_6$H$_4$O)$_2$, FTC-Aca-Ala-Ala-Ala-Phe$^P$(OPh)$_2$ can also be prepared by the coupling of FTC-Aca-OH and H-Ala-Ala-Ala-Phe$^P$(OPh)$_2$, FTC-Aca-Ala-Ala-Ala-Ala-Phe$^P$(4-Cl-C$_6$H$_4$O)$_2$ can be obtained from the reaction of FTC-Aca-OH and H-Ala-Ala-Ala-Phe$^P$(4-Cl-C$_6$H$_4$O)$_2$, FTC-Aca-Ala-Ala-Pro-Phe$^P$(OPh)$_2$ can be prepared from the reaction of FTC-Aca-OH and H-Ala-Ala-Pro-Phe$^P$(Oph)$_2$, FTC-Aca-Ala-Ala-Pro-Phe$^P$(4-Cl-C$_6$H$_4$O)$_2$ can be prepared from the reaction of FTC-Aca-OH and H-Ala-Ala-Pro-Phe$^P$(4-Cl-C$_6$H$_4$O)$_2$, the procedure described above can also be used to prepare FTC-Aca-Phe-Pro-Phe$^P$(Oph)$_2$ from FTC-Aca-OH and H-Phe-Pro-Phe$^P$(OPh)$_2$, FTC-Aca-Phe-Pro-Phe$^P$(4-Cl-C$_6$H$_4$O)$_2$ can be obtained from the reaction of FTC-Aca-OH and H-Phe-Pro-Phe$^P$(4-Cl-C$_6$H$_4$O)$_2$, FTC-Aca-Val-Pro-Phe$^P$(OPh)$_2$ can be obtained from the reaction between FTC-Aca-OH and H-Val-Pro-Phe$^P$(OPh)$_2$, and FTC-Aca-Val-Pro-Phe$^P$(4-Cl-C$_6$H$_4$O)$_2$ can be prepared following the same procedure from FTC-Aca-OH and H-Val-Pro-Phe$^P$(4-Cl-C$_6$H$_4$O)$_2$.

EXAMPLE 5

Diphenyl 1-(6-(5-fluoresceinylthiocarbamoylamino) caproylamino)(4-amidinophenyl) methanephosphonate (FTC-Aca-(4-AmPh)Gly$^P$ (OPh)$_2$)

FTC-Aca-OH (0.20 g, 0.38 mmol), (4-AmPh)Gly$^P$(OPh)$_2$.HCl (0.19 g, 0.42 mmol) were dissolved in 10 mL of DMF in a 25 mL round bottom flask. N-methylmorpholine (NMM) (0.05 mL) was added to the flask followed by HOBt (0.05 g, 0.38 mmol). The flask was cooled in an ice bath for 15 min then DCC (0.08 g, 0.38 mmol) was added and the mixture was stirred in ice for 5 h and at RT for 48 h. The solvent was removed in vacuo and the residue was purified on a silica gel preparative plate using CHCl$_3$:MeOH:HOAc (16:6:1). The product was isolated as a yellow oil that was dissolved in saturated HCl in ethyl acetate. The solvent was removed immediately after dissolution and the residue was then triturated with hexane to give a yellow solid: yield 15–20%; TLC, major spot (R$_f$=0.44, CHCl$_3$:MeOH:HOAc, 16:6:1); the $^1$H NMR spectrum is consistent with the structure of this compound and it showed the presence of some impurities; MS (FAB$^+$) m/e 884 ((M-HCl)+1). Anal. calcd. for C$_{47}$H$_{43}$N$_5$O$_9$ClPS.5H$_2$O: C, 55.87; H, 5.28; N, 6.93; S, 3.17. Found: C, 56.25; H, 5.47; N, 7.32; S, 3.38.

Using the same procedure FTC-Aca-(4-AmPh)Gly$^P$(4-Cl-C$_6$H$_4$O)$_2$ be prepared from the reaction of FTC-Aca-OH and H-(4-AmPh)Gly$^P$(4-Cl-C$_6$H$_4$O)$_2$, FTC-Aca-Pro-(4-AmPh)Gly$^P$(OPh)$_2$ can also be prepared following this procedure from FTC-Aca-OH and H-Pro-(4-AmPh)Gly$^P$(OPh)$_2$, FTC-Aca-Phe-Pro-(4-AmPh)Gly$^P$(OPh)$_2$ can be obtained from the reaction between FTC-Aca-OH and H-Phe-Pro-(4-AmPh)Gly$^P$(OPh)$_2$, FTC-Aca-Phe-Phe-(4-AmPh)Gly$^P$(OPh)$_2$ can be obtained from coupling FTC-Aca-OH to H-Phe-Phe-(4-AmPh)Gly$^P$(OPh)$_2$, FTC-Aca-Arg$^P$(OPh)$_2$ can be prepared from the reaction of FTC-Aca-OH and H-Arg$^P$(OPh)$_2$, and FTC-Aca-Lys$^P$(OPh)$_2$ can be prepared using the same procedure from FTC-Aca-OH and H-Lys$^P$(OPh)$_2$.

EXAMPLE 6

6-(4(or 2)(9-(2,3,6,7,12,13,16,17-octahydro-1H,5H, 11H,15H-xantheno(2,3,4-ij:5,6,7-i'j')diquinolizinyl-18-ium))3(or 5)-sulfo-1-phenylsulfonamido)caproic Acid, Hydroxide, Inner Salt (TXR-Aca-OH)

The intermediate TXR-Aca-OMe was synthesized from a freshly prepared dry Texas Red solution in CHCl$_3$ (Titus et al., 1982) and 1 equivalent of 6-aminocaproic acid methyl ester in the presence of 1 equivalent NMM. After stirring at 0° C. for 0.5 h and at RT overnight, the mixture was concentrated in vacuo to give a dark solid that was purified on a silica gel preparative plate using CHCl$_3$:MeOH:HOAc (16:3:1) to give TXR-Aca-OMe: yield, 67%; one spot on TLC (R$_f$=0.71, CHCl$_3$:MeOH:HOAc, 16:3:1); $^1$H NMR (DMSO-d$_6$) d 8.42 (d, 1H), 7.98–7.85 (m, 2H), 7.35 (d, 1H), 6.52 (s, 2H), 3.60–3.40 (s and m, 11H), 3.05–2.95 (m, 4H), 2.92–2.80 (m, 2H), 2.67–2.55 (m, 4H), 2.27 (t, 2H), 2.11–1.75 (m, 8H), 1.55–1.18 (m, 6H); high resolution FAB-MS, m/e (M+H) calcd. 734.2570; found 734.2568. Anal. calcd. for C$_{38}$H$_{43}$N$_3$O$_8$S$_2$.2.5H$_2$O: C, 58.60; H, 6.21; N, 5.39; S, 8.23. Found: C, 58.41; H, 5.83; N, 5.33; S, 8.09.

An excess solution of 1N NaOH was added to TXR-Aca-OMe followed by a few drops of MeOH. The mixture was stirred at RT for 2 h, then cooled in an ice-bath. Concentrated HCl was added carefully until a dark solid completely precipitated. The solid was isolated by vacuum filtration and then purified on a preparative plate to give TXR-Aca-OH: yield, 85%; one spot on TLC ($R_f$=0.55, $CHCl_3$:MeOH:HOAc, 16:3:1); $^1$H NMR (DMSO-$d_6$) d 8.40 (d, 1H), 8.05–7.88 (m, 2H), 7.37 (d, 1H), 6.50 (s, 2H), 3.60–3.40 (m, 8H), 3.05–2.95 (m, 4H), 2.90–2.80 (m, 2H), 2.68–2.58 (m, 4H), 2.10–1.95 (m, 6H), 1.90–1.78 (m, 4H), 1.50–1.15 (m, 6H); high resolution FAB-MS m/e (M+H) calcd. 720.2435; found 720.2413.

EXAMPLE 7

Diphenyl 1-(6-(4(or 2)(9-(2,3,6,7,12,13,16,17-octahydro-1H,5H,11H,15H-xantheno(2,3,4-ij:5,6,7-i'j')diquinolizinyl-18-ium))3(or 5)sulfo-1-phenylsulfonamido)caproylphenylalanylleucylamino)-2-phenylethanephosphonate, Hydroxide, Inner Salt (TXR-Aca-Phe-Leu-Phe$^P$(OPh)$_2$)

This compound was prepared from TXR-Aca-OH (0.084 g, 0.12 mmol) and H-Phe-Leu-Phe$^P$(OPh)$_2$ hydrochloride (0.084 g, 0.13 mmol) using the DCC/HOBt method in the presence of TEA. The reaction was carried out in $CHCl_3$ at 0° C. for 2 h and at RT for 48 h. The crude product was purified on a silica gel preparative TLC plate using $CHCl_3$:MeOH:AcOH (16:3:1) as the eluting solvent. The isolated product was dissolved in 20 mL $CHCl_3$ and extracted twice with 10 mL of 5% aqueous $NaHCO_3$ then with 10 mL $H_2O$. The organic layer was dried ($Na_2SO_4$) and then concentrated to give a dark purple solid: yield, 25–35%; one spot on TLC, $R_f$=0.79, $CHCl_3$:MeOH:AcOH (16:3:1); NMR spectrum was recorded and was consistent with the proposed structure; high-resolution FAB-MS, m/e (M+H) calcd. 1315.501; found 1315.495. Anal. calcd. for $C_{72}H_{79}N_6O_{12}PS_2 \cdot 2H_2O$: C, 63.98; H, 6.18; N, 6.22; S, 4.74. Found: C, 63.62; H, 6.03; N, 6.39; S, 4.87.

This procedure can be used to prepare TXR-Aca-Ala$^P$(OPh)$_2$, TXR-Aca-Met$^P$(OPh)$_2$, TXR-Aca-Phe$^P$(OPh)$_2$, and TXR-Aca-(4-AmPh)Gly$^P$(OPh)$_2$ from coupling TXR-Aca-OH with H-Ala$^P$(OPh)$_2$, H-Met$^P$(OPh)$_2$, H-Phe$^P$(OPh)$_2$, and H-(4-AmPh)Gly$^P$(OPh)$_2$, respectively. Likewise TXR-Aca-Pro-Phe$^P$(OPh)$_2$ and TXR-Aca-Pro-Phe$^P$(OPh)$_2$ can be prepared from coupling TXR-Aca-OH with H-Pro-Phe$^P$(OPh)$_2$ and H-Leu-Phe$^P$(OPh)$_2$, respectively. TXR-Aca-Ala-Met$^P$(OPh)$_2$ can be obtained from the reaction between TXR-Aca-OH and H-Ala-Met$^P$(OPh)$_2$. TXR-Aca-Phe-Leu-Phe$^P$(4-Cl-$C_6H_4$O)$_2$ can be prepared from TXR-Aca-OH and H-Phe-Leu-Phe$^P$(4-Cl-$C_6H_4$O)$_2$, TXR-Aca-Ala-Ala-Ala-Phe$^P$(OPh)$_2$ can be obtained from the reaction between TXR-Aca-OH and H-Ala-Ala-Ala-Phe$^P$(OPh)$_2$, TXR-Aca-Ala-Ala-Ala-Phe$^P$(4-Cl-$C_6H_4$O)$_2$ can also be prepared from the reaction of TXR-Aca-OH and H-Ala-Ala-Ala-Phe$^P$(4-Cl-$C_6H_4$O)$_2$, TXR-Aca-Ala-Ala-Pro-Phe$^P$(OPh)$_2$ can be obtained from coupling TXR-Aca-OH to H-Ala-Ala-Pro-Phe$^P$(OPh)$_2$, TXR-Aca-Ala-Ala-Pro-Phe$^P$(4-Cl-$C_6H_4$O)$_2$ can be prepared from the reaction between TXR-Aca-OH and H-Ala-Ala-Pro-Phe$^P$(4-Cl-$C_6H_4$O)$_2$, TXR-Aca-Phe-Pro-Phe$^P$(OPh)$_2$ can be obtained from the reaction between TXR-Aca-OH and H-Phe-Pro-Phe$^P$(OPh)$_2$, TXR-Aca-Phe-Pro-Phe$^P$(4-Cl-$C_6H_4$O)$_2$ can also be obtained from coupling TXR-Aca-OH to H-Phe-Pro-Phe$^P$(4-Cl-$C_6H_4$O)$_2$, TXR-Aca-Val-Pro-Phe$^P$(OPh)$_2$ can be prepared by this procedure from TXR-Aca-OH and H-Val-Pro-Phe$^P$(OPh)$_2$, TXR-Aca-Val-Pro-Phe$^P$(4-Cl-$C_6H_4$O)$_2$ can be prepared from the reaction between TXR-Aca-OH and H-Val-Pro-Phe$^P$(4-Cl-$C_6H_4$O)$_2$, TXR-Aca-Ala-Ala-Ala$^P$(OPh)$_2$ can be obtained from coupling TXR-Aca-OH to H-Ala-Ala-Ala$^P$(OPh)$_2$, TXR-Aca-Ala-Ala-Met$^P$(OPh)$_2$ can also be prepared from the reaction of TXR-Aca-OH with H-Ala-Ala-Met$^P$(OPh)$_2$, and TXR-Aca-(4-AmPh)Gly$^P$(OPh)$_2$ can be prepared following the same procedure from the reaction between TXR-Aca-OH and H-(4-AmPh)Gly$^P$(OPh)$_2$.

What is claimed is:

1. A compound of the formula:

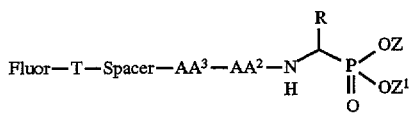

or an acceptable salt, wherein

Fluor is selected from the group consisting of

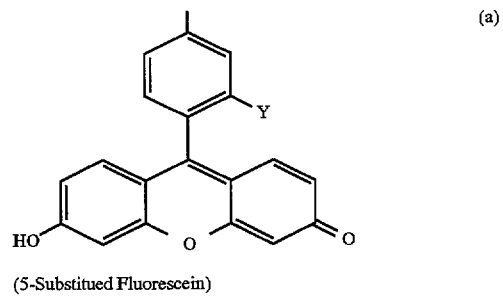

(5-Substitued Fluorescein)

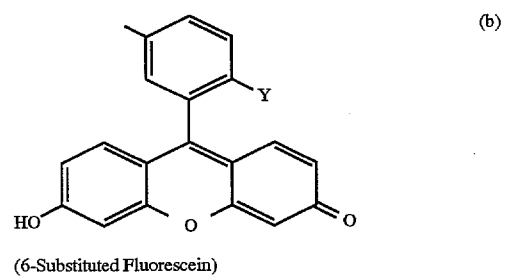

(6-Substituted Fluorescein)

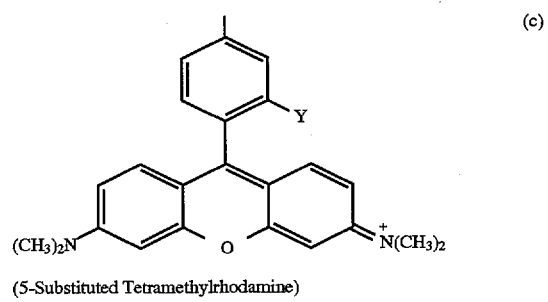

(5-Substituted Tetramethylrhodamine)

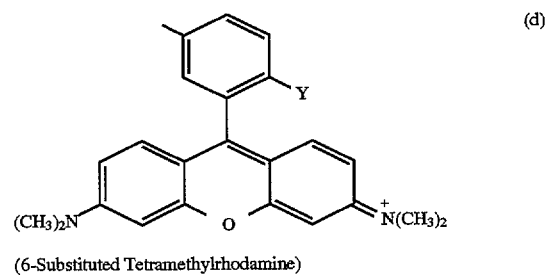

(6-Substituted Tetramethylrhodamine)

-continued

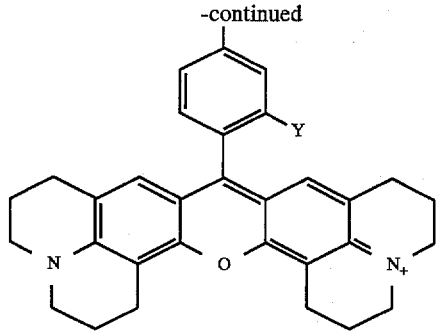

(5-Substituted Texas Red) (e)

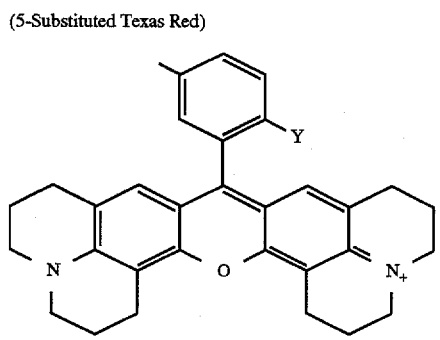

(6-Substituted Texas Red) (f)

and (g) an aromatic fluorescent group with an emission maximum of 350 to 700 nm, Y is selected from the group consisting of H, COOH, and $SO_3H$, T is selected from the group consisting of —NH—CO—, —NH—CS—, —CO—, and —$SO_2$—, Spacer is selected from the group consisting of
(a) a single bond,
(b) —NH—$CH_2$—$CH_2$—$CH_2$—$CH_2$—$CH_2$—CO—,
(c) —NH—$CH_2$—$CH_2$—$CH_2$—$CH_2$—$CH_2$—CO—NH—$CH_2$—$CH_2$—$CH_2$—$CH_2$—$CH_2$—CO—,
(d) an organic structure which is 3-24 Å long and including a backbone comprising at least one member of the group consisting of —$CH_2$—$CH_2$—, —CO—NH—, —NH—CO—, —$CH_2$—CO—, —$CH_2$—NH—, —NH—$CH_2$—, and —$C_6H_4$—, $AA^3$ and $AA^2$ are the same or different and are selected independently from the group consisting of
(a) a single bond,
(b) a side chain blocked or unblocked amino acid residue with the L or D configuration at the α-carbon selected from the group consisting of alanine, valine, leucine, isoleucine, proline, methionine, methionine sulfoxide, methionine sulfone, phenylalanine, tryptophan, serine, threonine, cysteine, tyrosine, asparagine, glutamine, aspartic acid, glutamic acid, lysine, arginine, histidine, phenylglycine, norleucine, norvaline, alpha-aminobutyric acid, citrulline, hydroxyproline, ornithine, and homoarginine, and
(c) glycine, sarcosine, epsilon-aminocaproic acid, and beta-alanine, R is selected from the group consisting of
(a) the side chain of a blocked or unblocked amino acid side chain selected from the group consisting of glycine, alanine, valine, leucine, isoleucine, proline, methionine, methionine sulfoxide, methionine sulfone, phenylalanine, tryptophan, serine, threonine, cysteine, tyrosine, asparagine, glutamine, aspartic acid, glutamic acid, lysine, arginine, histidine, phenylglycine, norleucine, norvaline, alpha-aminobutyric acid, citrulline, hydroxyproline, ornithine, and homoarginine, and
(b) phenyl substituted with B, benzyl substituted with B on the phenyl,
B is selected from the group consisting of amidino (—C(=NH)$NH_2$), guanidino (—NH—C(=NH)$NH_2$), isothiureido (—S—C(=NH)$NH_2$), and amino, Z and $Z^1$ are the same or different and are selected independently from the group consisting of phenyl, phenyl substituted with J, phenyl disubstituted with J, and phenyl trisubstituted with J, and J is selected from the group consisting of halogen, $C_{1-6}$ alkyl, $C_{1-6}$ perfluoroalkyl, $C_{1-6}$ alkoxy and CN.

2. A compound according to claim 1 wherein

Fluor is the structure

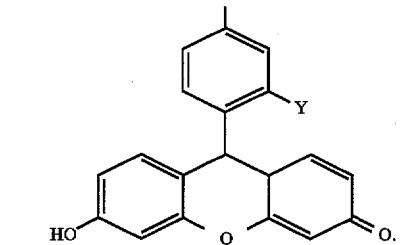

3. A compound according to claim 2 wherein

Y is COOH,

T is selected from the group consisting of —NH—CS— and —NHCO—,

Spacer is —NH—$CH_2$—$CH_2$—$CH_2$—$CH_2$—$CH_2$—CO—, $AA^3$ and $AA^2$ are the same or different and are selected independently from the group consisting of
(a) a single bond,
(b) a blocked or unblocked amino acid residue with the L or D configuration at the α-carbon selected from the group consisting of alanine, valine, leucine, isoleucine, methionine, phenylalanine, and proline, R is selected from the group consisting of
(a) the side chain of a blocked or unblocked amino acid residue selected from the group consisting of alanine, valine, leucine, isoleucine, methionine, phenylalanine, aspartic acid, lysine, arginine, and phenylglycine,
(b) a phenyl group substituted with B,
B is amidino, and Z and $Z^1$ are the same or different and are selected independently from the group consisting of phenyl or phenyl substituted with a halogen.

4. A compound according to claim 1 wherein

Fluor is the structure

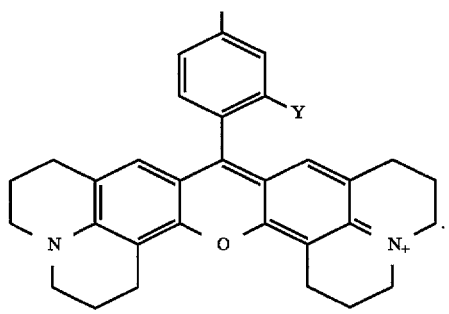

5. A compound according to claim 4 wherein
Y is $SO_3H$,
T is selected from the group consisting of $-SO_2-$ and $-NHCS-$,
Spacer is $-NH-CH_2-CH_2-CH_2-CH_2-CH_2-CO-$,
$AA^3$ and $AA^2$ are the same or different and are selected independently from the group consisting of (a) a single bond,
(b) a blocked or unblocked amino acid residue with the L or D configuration at the α-carbon selected from the group consisting of alanine, valine, leucine, isoleucine, methionine, phenylalanine, and proline, R is selected from the group consisting of
(a) the side chain of a blocked or unblocked amino acid side chain selected from the group consisting of alanine, valine, leucine, isoleucine, methionine, phenylalanine, aspartic acid, lysine, arginine, and phenylglycine,
(b) a phenyl group substituted with B, B is amidino, and Z and $Z^1$ are the same or different and are selected independently from the group consisting of phenyl or phenyl substituted with a halogen.

6. A compound or an acceptable salt of the compound selected from the group of structures consisting of (a)
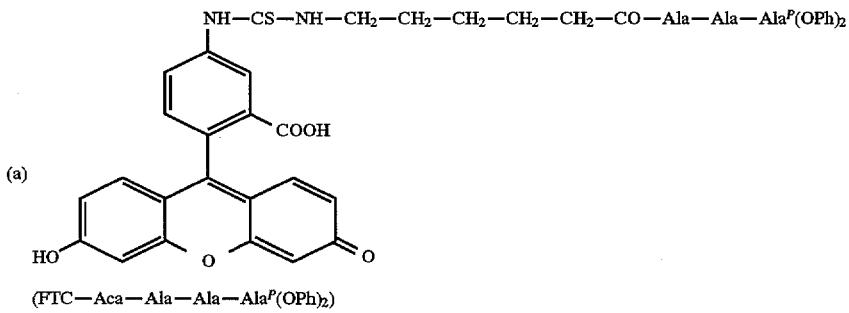
(FTC—Aca—Ala—Ala—Ala$^P$(OPh)$_2$)

(b)
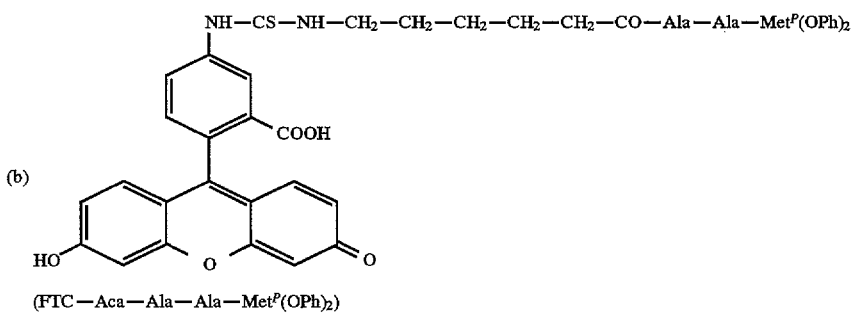
(FTC—Aca—Ala—Ala—Met$^P$(OPh)$_2$)

(c)
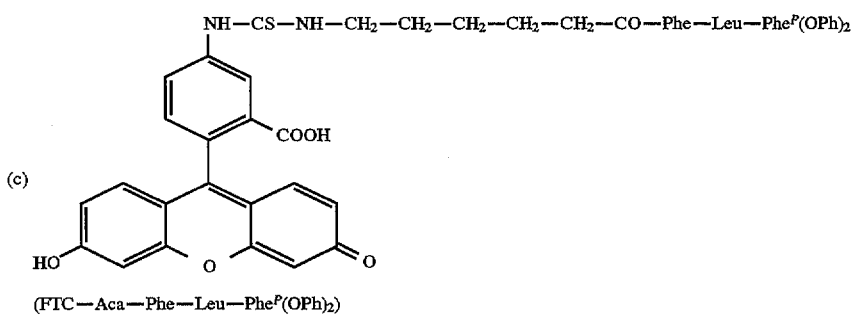
(FTC—Aca—Phe—Leu—Phe$^P$(OPh)$_2$)

-continued

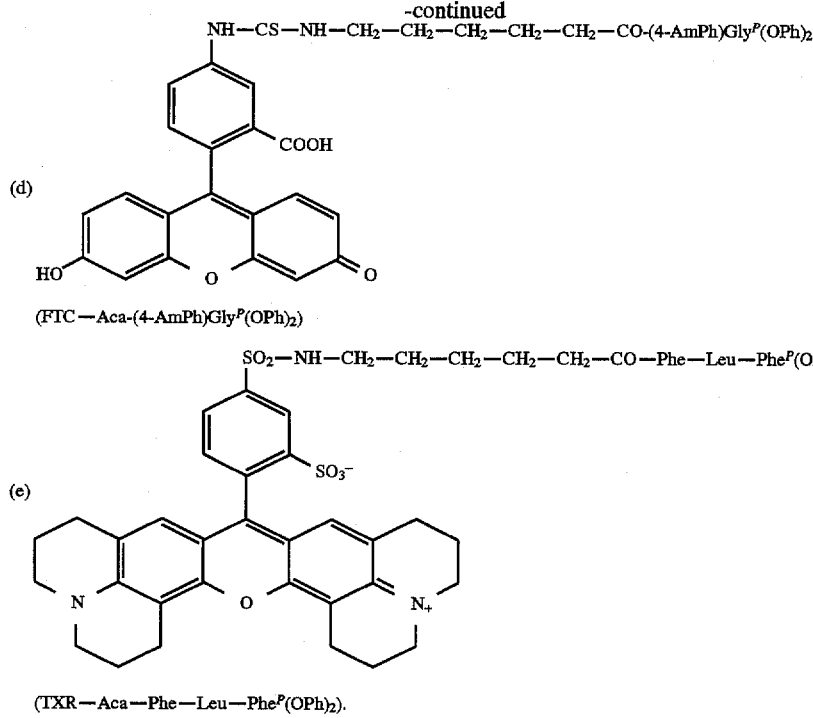

7. A compound according to claim 1 wherein $AA^3$ is a side chain unblocked amino acid residue with the L configuration at the α-carbon.

8. A compound according to claim 1 wherein $AA^3$ is a side chain unblocked amino acid residue with the D configuration at the α-carbon.

9. A compound according to claim 1 wherein $AA^3$ is a side chain blocked amino acid residue with the L configuration at the α-carbon.

10. A compound according to claim 1 wherein $AA^3$ is a side chain blocked amino acid residue with the D configuration at the α-carbon.

11. A compound according to claim 1 wherein $AA^2$ is a side chain unblocked amino acid residue with the L configuration at the α-carbon.

12. A compound according to claim 1 wherein $AA^2$ is a side chain unblocked amino acid residue with the D configuration at the α-carbon.

13. A compound according to claim 1 wherein $AA^2$ is a side chain blocked amino acid residue with the L configuration at the α-carbon.

14. A compound according to claim 1 wherein $AA^2$ is a side chain blocked amino acid residue with the D configuration at the α-carbon.

15. A compound according to claim 1 wherein $AA^3$ and $AA^2$ are the same.

16. A compound according to claim 1 wherein $AA^3$ and $AA^2$ are different.

17. A compound according to claim 1 wherein Z and $Z^1$ are the same.

18. A compound according to claim 1 wherein Z and $Z^1$ are different.

19. A method for detecting the presence of a serine protease in cells, plasma, or other biological media, comprising contacting the serine protease with a compound according to claim 1.

20. A method for inhibiting a serine protease that is present in cells, plasma, or other biological media, comprising contacting the serine protease with a compound according to claim 1.

* * * * *